United States Patent [19]

Ashikawa et al.

[11] Patent Number: 5,107,066
[45] Date of Patent: Apr. 21, 1992

[54] METHOD OF PRODUCING POTATO CYST NEMATODE HATCHING STIMULUS

[75] Inventors: Ikuo Ashikawa, Tsukuba; Akio Murai; Akio Fukuzawa, both of Sapporo; Masato Koshi, Tokyo; Hiroshi Kamada, Tsukuba, all of Japan

[73] Assignee: Harima Chemicals, Inc., Kakogawa, Japan

[21] Appl. No.: 746,096

[22] Filed: Aug. 12, 1991

Related U.S. Application Data

[63] Continuation of Ser. No. 629,846, Dec. 19, 1990.

[30] Foreign Application Priority Data

Dec. 21, 1989 [JP] Japan ................. 1-329434
Oct. 2, 1990 [JP] Japan ................. 2-263209

[51] Int. Cl.$^5$ ............... C12N 15/00; C12N 1/20; C12R 1/41
[52] U.S. Cl. .................. 800/205; 424/DIG. 12; 435/41; 435/171; 435/240.4; 435/240.54; 435/252.2; 435/253.3; 435/253.6; 435/172.3; 935/30; 935/56; 935/64; 935/67
[58] Field of Search ............... 424/93, DIG. 12; 435/41, 171, 253.6, 252.3, 240.54, 252.2, 240.4; 800/205; 935/30, 56, 67, 64

[56] References Cited

U.S. PATENT DOCUMENTS

| | | | |
|---|---|---|---|
| 3,581,686 | 6/1971 | Raymond | 514/765 |
| 4,036,987 | 7/1977 | Thompson et al. | 514/671 |
| 4,073,939 | 2/1978 | Thompson et al. | 514/625 |
| 4,273,768 | 6/1981 | Kochansky et al. | 514/141 |
| 4,658,082 | 4/1987 | Simpson et al. | 435/320.1 |
| 4,801,154 | 1/1989 | Stuart et al. | 435/240.95 |
| 4,863,863 | 9/1989 | Cocking et al. | 435/172.2 |
| 4,886,753 | 12/1989 | Marcker et al. | 435/172.3 |
| 4,990,607 | 2/1991 | Katagiri et al. | 435/172.3 |

FOREIGN PATENT DOCUMENTS

1272989 11/1989 Fed. Rep. of Germany.
0237784 10/1988 Japan.
0245687 10/1988 Japan.
0254982 10/1988 Japan.

OTHER PUBLICATIONS

DPerwent Abs. 87-300111/43 Kamata et al. DE 3706978 (Oct. 1987).
Biotech Abs 87-01445 (J61221140) Oct. 1986.
Biotech Abs 86-02352 Ooms et al. PMBIDB "Plant Mol. Biol", (1985) 5,4, 205-212.
Patent Abstracts of Japan unex.applns. C field vol. 7, No. 143, Jun. 22, 1983; The Patent Office Japanese Government p. 58 C172 Kokai No. 58-55 493.
Patent Abstracts of Japan, unexamined applications C field, vol. 13, No. 49 Feb. 3, 1989, The Patent Office Japanese Government p. 153 C 565 Kokai-No. 63-245 687 (Tsumura & Co.).
Patent Abstracts of Japan, unexamined applications, C Filed, vol. 13, No. 63, Feb. 13, 1989, Kokai No. 63-254-982.

*Primary Examiner*—Herbert J. Lilling
*Attorney, Agent, or Firm*—Cushman, Darby & Cushman

[57] ABSTRACT

Disclosed is a novel method for the production of a substance which accelerates the hatching of potato cyst nematode eggs using root cells of plants of Solanaceae family.

In this method, the cultivation of the root cells may be carried out in a specific medium, or, alternatively, the cells obtained by transformation of the root cells with Ri plasmid T-DNA is used.

The disclosed method can be applied for the prevention of the damage by the cyst nematodes in potato cultivation.

5 Claims, No Drawings

METHOD OF PRODUCING POTATO CYST NEMATODE HATCHING STIMULUS

This is a continuation of application No. 07/629,846, filed on Dec. 19, 1990

FIELD OF THE INVENTION

The present invention relates to a method of producing a substance for stimulating hatching of potato cyst nematodes (cisto nematoda), which comprises the biosynthesis in plants of Solanaceae family by means of an organ culture of roots of plants of Solanaceae family.

DESCRIPTION OF THE PRIOR ART

The potato cyst nematode (*Globodera rostochiensis*) is one of harmful worms in agriculture, which is parasitic on the plant of Solanaceae family such as potato and tomato, and the damage is particularly serious in European countries. In this nematode, a female imago turns into a cyst maintaining eggs inside the body. The eggs are protected from various exterior adverse conditions (low temperature and dryness) so as to exert extreme stability; thus it is so far believed to be almost impossible to destroy the dormant larvae within the eggs, which are protected by the cyst and shells, by the use of agricultural chemicals.

One of the characteristics of the nematode is that the hatching (termination of its dormant stage) is stimulated by a chemical substance secreted from the roots of the parasitic plants. This fact has already been found by Bannacke, but the responsible substance has not been identified up to date.

This substance (or an extract containing this substance) can be applicable as an agricultural chemical for against the potato cyst nematodes. Namely, if this substance is distributed on a field in autumn after host plants die off or in spring when the host plants are not yet planted in the field, the dormant stage of the eggs of the cyst nematode is disturbed and the hatching starts. Consequently, the resultant hatched larvae cannot survive in the absence of the host to parasitize.

Recently, techniques for production of such valuable substances which is produced by plants, using tissue cultures of plants, have been considerably established. By culturing plant calluses, the valuable substances can be obtained in a short period of time without waiting the growth of corresponding natural plants. The production of shikonin by the callus culture of gromwell (*Lithospermum ervthrorhizon*) has already been industrialized.

However, in general, it is difficult to produce the substances, which are specifically produced by plant organs, by using callus cultures. For the production of such substances, cultures of plant organs are applicable.

For example, substances which are produced specifically in roots are produced by root cultures. Several attempts have already been made to obtain substances which are produced in plant roots using cultured roots (Japanese Patent Published No. 245687/1988, Japanese Patent Published No. 237784/1988).

On the other hand, it is known that hairy roots are induced when dicotyledonous plants are infected with *Agrobacterium rhizogenes*. These hairy roots are transformed ones which grow extremely fast as compared to corresponding untransformed roots and, in addition, are potentially able to produce root-derived secondary metabolites and thus suitable for industrial production of substances which are to be produced specifically in roots. Examples of the substances produced using hairy roots includes shikonin (Japanese patent Published No. 133995/1988) and ginsenosides (Japanese Patent Published No. 254982/1988).

The Means to Solve the Problem

Cultured roots of plants of Solanaceae family can be obtained by the following methods:

1. Seeds of plants are aseptically sown on a solid medium for plant culture for germination, and then the roots of the seedlings are excised and subcultured on the medium.

The medium used herein contains a carbon source, nitrogen sources, mineral salts, metals in a trace amount, vitamins and others.

Examples of the carbon source include carbohydrates or fatty acid derivatives. Examples of the preferable carbon source include glucose, sucrose and analogs thereof Examples of the nitrogen source include nitrate ions, ammonium ions and amino acids. Examples of the mineral salts include phosphates, chlorides and sulfates Known examples of preferable media include Murashige-Skoog medium, Gamborg medium, White medium, Linsmaier-Skoog medium and Heller medium.

Phytohormones may be added to the above-mentioned media if necessary.

Furthermore, in order to produce a solid medium, for example, agar at a concentration of 0.1%-2% by weight is added to an ordinary fluid medium. In this case ammonium ion is not removed since the germination of seeds is aimed at.

2. A part of a plant is cut off, sterilized and then placed on a medium with or without phytohormones. Adventitious roots generated from the plant are cut off and subcultured on the medium.

3. A part of a plant is cut off, sterilized and then planted on a medium with phytohormones.

After several weeks, calluses are induced from the plant segment and furthermore adventitious roots are induced from the calluses. These adventitious roots are cut off and then subcultured on the medium.

Some of the cultured roots of the plants obtained according to the above-mentioned method can be grown eternally by subculturing on a medium with or without hormones.

In order to efficiently produce a substance to promote the hatching of potato cyst nematodes, cultured roots of plants of Solanaceae family, which have been subcultured on a solid medium, are inoculated in a liquid medium for culturing. The medium to be used primarily contains, as to the inorganic component of the medium except for inorganic nitrogen, constituents of any known inorganic salt synthetic medium supplemented with vitamins, amino acids and organic substances or the like. The present invention is also characterized in that the medium to be used contains 10-100 mM nitrate ion and no ammonium ion as to the inorganic nitrogen source. The amount of the substance for stimulating hatching of potato cyst nematodes, which is produced in the cultured roots, decreases in a medium containing ammonium ion.

When hairy roots are employed, plants of Solanaceae family are treated with *Agrobacterium rhizogenes* and the induction is carried out by transforming the plant cells by T-DNA of Ri-plasmid. In the present invention, any Solanaceae plant can be used; however, the plants which belong to genus Lycopersicon or Solanum are preferably used.

Examples of Agrobacterium rhizogenes used for forming hairy roots in these plants include:
Agrobacterium rhizogenes 15834 (ATCC 15834)
Agrobacterium rhizogenes A4 (ATCC 43057)

According to the present invention, when plants are treated with *Agrobacterium rhizogenes*, T-DNA in the Ri-plasmid of *A. rhizogenes* is introduced (transformed) in the nucleus DNA of the plant cells.

In order to introduce the Ri-plasmid T-DNA in stalks, roots, leaves or calluses of the above-mentioned plants of Solanaceae family to obtain the transformed hairy roots, for example, the following methods can be used.
1. A method of direct inoculation to the plants
2. A leaf disk method using leaf segments (e.g., R. B. Horsh et al. Science 227, 1229, 1985)

The T-DNA is introduced by the above-mentioned method and then Agrobacterium is removed from the hairy-roots. The bacteria were removed by subculturing on media containing antibiotics.

The hairy roots thus obtained are cultured aseptically on an ordinary medium for tissue culture. The medium used for the culture contains a carbon source, nitrogen sources, mineral salts, metal in trace, vitamins and so forth.

Examples of the carbon source are carbohydrates or fatty acid derivatives. Examples of the preferable carbon source include glucose, sucrose and analogues thereof. Examples of the nitrogen source include nitrate ion, ammonium ion and amino acids. Examples of mineral salts include phosphates, chlorides and sulfates. Known examples of preferable media include Murashige-Skoog medium, Gamborg medium, White medium Linsmaier-Skoog medium and Heller medium.

Phytohormones may be added to the above-mentioned media if necessary.

The amount of plants to be inoculated onto a medium varies in a wide range; however, in general, about 10 mg to about 1 g fresh weight of either cultured roots or hairy roots per 50 ml of a fluid medium is preferably inoculated.

In the present invention, the cultivation is carried out at about 10° C. to about 35° C., preferably at 23° C. to 28° C. A substance for stimulating the hatching of potato cyst nematodes is produced and accumulated in the medium or in the cultured roots after the completion of the cultivation.

A test for the secretion of the substance for stimulating the hatching of potato cyst nematodes into the fluid medium is carried out as follows: Cysts of potato cyst nematodes were sieved from cyst-containing field soil. The cysts are stored in water for about 10 days. The temperature is preferably at 25° C. The outer shells of the stored cysts are broken using a bamboo spit so as to discharge the eggs. The eggs are sifted out with a sieve and about 100 eggs each are placed on a Syracuse lens dish. A fluid in which the above-mentioned root culture solution is appropriately diluted and water are added to this lens dish to make the final volume to 10 ml. The dilutions of the cultured medium are made generally in the range of 1/10 to 1/100,000. An egg suspension with this solution to be tested is allowed to stand in an incubator at 25° C., and after 10 days the hatching is observed using a microscopy to calculate the hatching rate (%).

EXAMPLE 1

Seeds of the tomato plant (*Lycopersicon esculentum*) were sterilized with a bactericide such as sodium hypochlorite and then sown on Murashige-Skoog (MS) solid medium containing 3% sucrose. The root tip segments of the germinated sterile plant were excised and then subcultured on MS solid medium to prepare tomato cultured roots.

Fifty milliliters each of a ½ MS liquid medium (A) in which concentrations of major salts in MS were reduced to ½ and a modified MS liquid medium (modified ½ MS, B) in which all the nitrogen components of the major salts, except ammonium ion, were replaced by $KNO_3$ was placed in a 200-ml volume of Erlenmeyer flask and then sterilized at 120° C. for 15 minutes. On each of these liquid media, about 100 mg of the above-mentioned tomato cultured roots was inoculated and then cultured at 25° C. for 20 days with shaking (rotating at 70 rpm/minute).

When the cultured roots were cultured in the ½ MS medium (A), the hatching activity was observed up to 1000-fold dilutions; when cultured in the modified ½ MS medium (B), the production of the hatching accelerating substance increased about ten times so that the hatching activity was observed even when the medium was diluted 10,000 times.

On the other hand, in order to detect the hatching substance remaining in the cultured roots after the cultivation, the cultured roots cultivated in the modified ½ MS medium were homogenized in 10 ml of water and then the supernatant was taken for the determination of the hatching activity The hatching activity was observed down to the 1/1,000 dilution (Table 1). This value is considerably low as compared to that observed in the medium after cultivation, which indicates that the hatching stimulus is mostly released from the roots to the medium.

TABLE 1

Hatching rates (%) in tomato cultured root media and in cultured root extract

|  | 1/100 | 1/1000 | 1/10000 | 1/100000 |
|---|---|---|---|---|
| ½ MS liquid medium (A) | 84.9 | 55.5 | 20.0 | 25.0 |
| Modified ½ MS liquid medium (B) | 79.1 | 78.7 | 50.7 | 22.8 |
| Cultured root extract | 71.2 | 60.5 | 27.0 | 16.9 |

EXAMPLE 2

(1) Tomato hairy roots

Seeds of the tomato plant (*Lycopersicon esculentum*) were sterilized with a bacericide such as sodium hypochlorite and then seeded on a Murashige-Skoog (MS) solid medium containing 3% sucrose. Stems of the sterile seedlings were inoculated with *Agrobacterium rhizogenes* A4 (ATCC 43057) carrying Ri-plasmid.

After 2 to 4 weeks, the hairy roots generated from the inoculation site were excised, transferred on an MS solid medium containing 0.5 g/l of claforan and then transferred to a fresh medium of the same composition after 1 to 2 weeks. This procedure was repeated 2 to 3 times and then the sterile hairy roots were obtained.

Fifty milliliters each of a ½ MS liquid medium in which concentrations of the major salts in MS were reduced to ½ and an MS liquid medium was placed in a 200-ml volume of Erlenmeyer flask and then sterilized at 120° C. for 15 minutes. On each of these fluid media 20 mg of the above-mentioned hairy roots was inoculated and then cultured at 25° C. for 20 days with shaking (rotating at 70 rpm/minute).

The medium after the cultivation was diluted with water and then added to the suspension of the eggs of potato cyst nematodes. The hatching activity in the suspension was observed.

The results (hatching rates) are shown in Table 2.

It is shown that the hatching activity was observed even when the medium was diluted 10,000 to 100,000 folds.

On the other hand, in order to detect the hatching stimulating substance remaining in the hairy roots after the cultivation, the hairy roots were homogenized in 10 ml of water and then the supernatant was taken for the determination of hatching activity. The hatching activity was observed in down to the 1/1,000 dilution (Table 1). However, the activity was extremely low as compared to that in the culture fluid after the cultivation, which indicates that the hatching stimulating substance is mostly released from the roots to the medium.

TABLE 2

Hatching rates (%) of tomato hairy root media and cultured root extract

|  | Dilution of fluid for detection | | | |
|---|---|---|---|---|
|  | 1/100 | 1/1000 | 1/10000 | 1/100000 |
| MS hairy root medium | 71.4 | 83.5 | 81.9 | 26.0 |
| ¼ MS hairy root medium | 71.2 | 79.8 | 58.9 | 70.6 |
| MS hairy root extract | 81.7 | 59.6 | 29.5 | 12.9 |

(2) Potato hairy roots

A stalk from the potato plant (*Solanum tuberosum*) in its early stage grown from the tuber of the plant was cut off, sterilized and infected with *Agrobacterium rhizogenes* A4 on the section of the stalk. When this stalk was grown aseptically on an MS medium, hairy roots were generated from the inoculation site 2 to 4 weeks after the infection. The hairy roots were excised and then subcultured on a solid MS medium for sterilization as described above for the tomato hairy roots.

The hairy roots were cultured in 50 ml of an MS fluid medium in a 200-ml volume of Erlenmeyer flask as described above for the tomato hairy roots. Table 3 shows the results of the test for their ability to hatch potato cyst nematodes.

Differing from the tomato hairy roots, the hatching stimulating substance is retained mostly in the roots rather than released in the medium.

TABLE 3

Hatching rates (%) of potato hairy root medium and cultured root extract

|  | Dilution of fluid for detection | | | |
|---|---|---|---|---|
|  | 1/100 | 1/1000 | 1/10000 | 1/100000 |
| MS hairy root medium | 73.9 | 56.1 | 28.5 | 16.7 |
| MS hairy root extract | 79.1 | 76.0 | 32.7 | 14.5 |

EFFECTS OF THE INVENTION

According to the present invention, a substance for stimulating the hatching of potato cyst nematodes is effectively produced from the plants of genus Solanaceae and genus Lycopersicon. The method of the present invention is extremely effective to exterminate this nematodes.

We claim:

1. A method of stimulating hatching of potato cyst nematode eggs comprising the steps of:
   i) introducing into a Solanaceae family plant T-DNA in a Ri-plasmid of Agrobacterium rhizogenes under conditions such that transformed root cells of the Solanaceae family plant are obtained;
   ii) cultivating said transformed root cells on a solid medium;
   iii) inoculating said cells with a liquid culture medium;
   iv) cultivating said cells;
   v) collecting the cultivated cell medium; and
   vi) contacting said medium with said eggs.

2. The method as set forth in claim 1, in which the plants of Solanaceae family are selected from those of genera Solanum and Lycopersicon.

3. The method as set forth in claim 1, in which the liquid culture medium contains 10–100 mM nitrate ions and no ammonium ion.

4. The method as set forth in claim 1, wherein said Agrobacterium are removed from said transformed root cells prior to cultivating in step (ii).

5. The method as set forth in claim 1, wherein said *Agrobacterium rhizogenes* is *Agrobacterium rhizogenes* 15834 (ATCC 15834) or *Agrobacterium rhizogenes* A4 (ATCC 43057).

* * * * *